United States Patent [19]

Knollmueller

[11] 4,329,486
[45] May 11, 1982

[54] PROCESS FOR PREPARING ALKOXYSILANE CLUSTER COMPOUNDS BY REACTING A TRIALKOXYSILANOL WITH AN AMIDATED ALKOXYSILANE CLUSTER COMPOUND

[75] Inventor: Karl O. Knollmueller, Hamden, Conn.

[73] Assignee: Olin Corporation, New Haven, Conn.

[21] Appl. No.: 278,225

[22] Filed: Jun. 29, 1981

[51] Int. Cl.$^3$ .......................... C07F 7/18; C07F 7/08; C07F 7/04
[52] U.S. Cl. ..................................... 556/458; 556/451
[58] Field of Search ................................ 556/451, 458

[56] References Cited

U.S. PATENT DOCUMENTS

| | | | |
|---|---|---|---|
| 2,758,126 | 8/1956 | Goldschmidt et al. | 260/448.8 |
| 2,758,127 | 8/1956 | Goldschmidt et al. | 260/448.8 |
| 3,965,135 | 6/1976 | Knollmueller | 556/458 |
| 3,965,136 | 6/1976 | Knollmueller | 260/448.8 A |
| 4,077,993 | 3/1978 | Knollmueller | 260/448.8 R |
| 4,175,049 | 11/1979 | Knollmueller | 556/451 X |

OTHER PUBLICATIONS

J. R. Wright et al., "Silicate Esters and Related Compounds, I. Synthesis of Certain Tetraalkoxysilanes, Polyalkoxysiloxanes, Bis-(trialkoxysilyl)-alkanes and Related Intermediates", *Journal of the American Chemical Society*, vol. 80, pp. 1733-1737, (Apr. 5, 1958).
C. R. Morgan et al., "Synthesis of Alkoxy Silanols and Siloxanes", *Journal of the American Chemical Society*, vol. 73, pp. 5193 and 5195, Nov. 1951.
Herbert H. Anderson, "Methylanilinosilanes and Ethylanilinosilanes; Reactions of Anilinosilanes", Journal of the American Chemical Society, vol. 73, pp. 5802 and 5803, Dec. 1951.
Herbert H. Anderson, "Dialkylaminogermanes and Dialkylaminosilanes", Journal of the American Chemical Society, vol. 74, pp. 1421-1423, Mar. 20, 1952.
Robert N. Scott et al., "Silicate Cluster Fluids", I & EC Product Research & Development, vol. 19, Mar. 1980, pp. 6-11.
Olin Corporation Product Bulletin for Silcate Cluster TM 102 Functional Fluid-Physical and Chemical Properties.
A Brief Synopsis of Olin Corporation's U.S. Patents Relating to Silicate Cluster TM Shielded Polysilicate Compounds and Methods of Their Preparation & Use.

*Primary Examiner*—Paul F. Shaver
*Attorney, Agent, or Firm*—William A. Simons; Thomas P. O'Day

[57] ABSTRACT

Described is a process for producing alkoxysilane cluster compounds by reacting a trialkoxysilanol with an amidated alkoxysilane cluster compound; this reaction being based on the following equation:

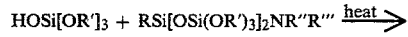

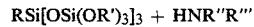

wherein R is hydrogen, an alkyl, an alkenyl, an aryl, or an aralkyl; each R' is independently selected from the same groups as R with the proviso that at least a majority of said R' radicals are sterically hindered alkyl groups having at least 3 carbon atoms; and R" and R''' are individually selected from hydrogen, lower alkyl groups having 1-4 carbon atoms, and phenyl.

9 Claims, No Drawings

PROCESS FOR PREPARING ALKOXYSILANE CLUSTER COMPOUNDS BY REACTING A TRIALKOXYSILANOL WITH AN AMIDATED ALKOXYSILANE CLUSTER COMPOUND

BACKGROUND OF THE INVENTION

1. Field of the Invention

This invention relates to a process for producing alkoxysilane cluster compounds.

2. Description of the Prior Art

U.S. Pat. No. 3,965,136, which issued to the present inventor on June 22, 1976, disclosed the preparation of alkoxysilane cluster compounds of the formula:

$$RSi[OSi(OR')_3]_3 \qquad (I)$$

wherein R is hydrogen, an alkyl, alkenyl, aryl, or aralkyl; and each R' is independently selected from the same groups as R with the proviso that at least a majority of the R' radicals are sterically hindered alkyl groups having at least 3 carbon atoms. These alkoxysilane compounds of formula (I) have been disclosed to be good functional fluids because of their unique combination of properties. Potential applications include high performance hydraulics, heat transfer agents, greases, dielectric coolants, and as a formulating aid in combination with other fluids.

In particular, two different processes for preparing these alkoxysilane cluster compounds are disclosed in U.S. Pat. No. 3,965,136. The first method of preparation involves the reaction of a trihalosilane with a trialkoxysilanol in the presence of an acid acceptor like pyridine. The second disclosed method of preparation involves the reaction of halosilane with an alkoxysilanol cluster compound in the presence of an acid acceptor.

An optimization of the above-noted first method of preparation is disclosed in U.S. Pat. No. 4,077,993, which also issued to the present inventor on Mar. 7, 1978. This improved method of preparation involves reacting a trihalosilane with a trialkoxysilanol in the presence of critical amounts of acceptor base and solvent reaction medium while maintaining the reaction temperature in a select range.

It has been found that these two methods for preparing alkoxysilane cluster compounds of formula (I) are somewhat hindered by the fact that they require an acid acceptor. Suitable acid acceptors such as pyridine are relatively expensive and must be recovered from the reaction mixture in order to reduce the cost of the synthesis. However, the recovery steps themselves are expensive to run on a large scale. Also, the yield of the alkoxysilane cluster product may be reduced because the occlusion of some of the product to the acid acceptor salt, even after washing steps. Furthermore, organic acid acceptors such as pyridine and the like have unpleasant physical characteristics and their use may present a health hazard in some circumstances.

Furthermore, it has been found that the use of certain trihalosilane intermediates does not result in desirably high yields of alkoxysilane cluster compounds for commercial use. The exact reasons for this is not known, but most likely involves steric hindrance of the reaction transition complexes of reactants and acid acceptor.

For the above and other reasons, a method for preparing alkoxysilane cluster compounds is needed which is relatively inexpensive and which does not require the use of pyridine or any other type of acid acceptor compound. The present invention, as described in detail below, presents a solution to this need.

Separately, polyalkoxy di-, tri-, and tetrasiloxanes have been prepared by reacting the corresponding alkoxysilanol with an appropriate alkoxysilamine. See U.S. Pat. No. 2,758,127, which issued to Goldschmidt et al on Aug. 7, 1956. However, this disclosed reaction was directed toward making linear-structured siloxanes, and not branched-structured compounds having sterically hindered alkoxy groups as is the present case.

BRIEF SUMMARY OF THE INVENTION

Therefore, the present invention is directed to a process for preparing an alkoxysilane cluster compound of the formula (I):

$$RSi[OSi(OR')_3]_3 \qquad (I)$$

wherein R is hydrogen, alkyl, alkenyl, aryl, or aralkyl; each R' is independently selected from the same groups as R with the proviso that at least a majority of said R' radicals are sterically hindered alkyl groups having at least 3 carbon atoms, comprising reacting a trialkoxysilanol of the formula (II):

$$HOSi[OR']_3 \qquad (II)$$

wherein R' is defined above, with an amidated alkoxysilane cluster compound of the formula (III):

$$RSi[OSi(OR')_3]_2NR''R''' \qquad (III)$$

wherein R and R' are defined above, and R'' and R''' are individually selected from hydrogen, lower alkyl groups having 1–4 carbon atoms and phenyl;

employing at least 0.8 moles of the trialkoxysilanol per one mole of the amidated alkoxysilane cluster compound;

and the reaction being carried out at about 60° C. to about 200° C.

DETAILED DESCRIPTION

The improved method for preparing alkoxysilane cluster compounds of formula (I) involves the reaction outlined in Equation (A) below between a trialkoxysilanol and an amidated alkoxysilane cluster compound:

$$HOSi[OR']_3 + RSi[OSi(OR')_3]_2NR''R''' \xrightarrow{heat} \qquad (A)$$
$$RSi[OSi(OR')_3]_3 + HNR''R'''$$

wherein R, R', R'' and R''' are as defined above.

The trialkoxysilanol reactants [represented by formula (II), above] and their methods of their preparation are disclosed in U.S. Pat. Nos. 4,198,346 and 4,207,247, both of which issued to the present inventor on Apr. 15, 1980, and June 10, 1980, respectively. The disclosures of these two U.S. patents are incorporated herein by reference in their entirety. However, these trialkoxysilanol reactants may be made by other known methods and the present invention is not to be limited to any such method of their preparation.

The preferred examples of these trialkoxysilanol reactants have R' radicals which are individually selected from hydrogen, alkyl or alkenyl groups having from 1 to about 18 carbon atoms, or aryl or aralkyl groups having about 6 to about 24 carbon atoms, subject to the proviso that at least a majority of the R' radicals are sterically hindered alkyl groups having 3 to about 18 carbon atoms. More preferably, all of the R' radicals of this reactant are sterically hindered alkyl groups having about 4 to about 12 carbon atoms. Most preferably, all of the R' radicals are sterically hindered alkyl groups derived from secondary or tertiary alcohols and having about 4 to about 12 carbon atoms. A specific example of the most preferred R' radical is a sec-butyl group.

Sterically hindered alkyl groups are defined as alkyl radicals which contribute to the hydrolytic stability of the molecule, i.e., which inhibit the reaction of water with silicon-oxygen or the carbon-oxygen bonds in the molecule. Exemplary of preferred sterically hindered alkyl R' radicals include (1) non-linear primary alkyl radicals having a beta position side chain of at least 2 carbons, (2) secondary alkyl radicals, and (3) tertiary alkyl radicals. However, it has now been found that cluster products of the present invention containing the R' radicals of the latter two classes (e.g., secondary alkyl groups such as sec-butyl and the like, and tertiary alkyl groups such as tert-butyl, 1,1-dimethylpropyl, 1,1-dimethylallyl and the like) are somewhat easier to prepare than cluster compounds of this invention containing the non-linear primary alkyl radicals (e.g., iso-butyl, 2-ethyl butyl, 2-ethyl pentyl, 3-ethyl pentyl, 2-ethyl hexyl, 2,4-dimethyl-3-pentyl, and the like).

Representative trialkoxysilanol reactants for the method of the present invention include those named in the following Table (I):

known methods and the present invention is not limited to any such method of their preparation.

The halogenated alkoxysilane cluster precursors and the method of their preparation are disclosed in U.S. Pat. No. 3,960,913, which issued to the present inventor on June 1, 1976. The disclosure of this U.S. Patent is incorporated herein by reference in its entirety.

Ammonia or amine precursors to the amidated alkoxysilane cluster reactants (III) are generally well known compounds and are made by many conventional methods.

In preferred embodiments of the present invention, the R radical on these amidated alkoxysilane cluster reactants includes either hydrogen, an alkyl or an alkenyl having 1 to 24 carbon atoms, or an aryl or an aralkyl having from about 6 to about 24 carbon atoms. More preferably, R is either hydrogen, an alkyl or alkenyl group having 1 to about 8 carbon atoms, or an aryl or aralkyl having about 6 to about 14 carbon atoms. Most preferably, R is either hydrogen or a lower alkyl group having 1 to 4 carbon atoms.

The R' groups of this reactant may generally and preferably be individually selected from the same groups as the R' groups of the trialkoxysilanol reactant. There is no necessity that the R' groups be the same for both reactants.

As stated above, the radicals R" and R'" on the amidated alkoxysilane cluster reactant are individually selected from hydrogen, lower alkyl groups having 1–4 carbon atoms, and phenyl groups. In preferred embodiments, R" and R'" are selected from either hydrogen, or a lower alkyl having 1 to 4 carbon atoms. More prefera-

TABLE I
REPRESENTATIVE TRIALKOXYSILANOLS

| Name | Chemical Formula |
|---|---|
| tri-isopropoxysilanol | [C$_3$H$_7$O]$_3$SiOH |
| tri-sec-butoxysilanol | [sec-C$_4$H$_9$O]$_3$SiOH |
| tri-tert-butoxysilanol | [tert-C$_4$H$_9$O]$_3$SiOH |
| di-(tert-butoxy) (sec-butoxy)silanol | [tert-C$_4$H$_9$O]$_2$[sec-C$_4$H$_9$O]SiOH |
| di(sec-butoxy) (isopropoxy)silanol | [sec-C$_4$H$_9$O]$_2$[C$_3$H$_7$O]SiOH |
| tri(3-pentaneoxy)silanol | [(CH$_3$CH$_2$)$_2$CHO]$_3$SiOH |
| tri-2-ethylhexoxysilanol | [C$_8$H$_{17}$O]$_3$SiOH |
| tri-2-ethylbutoxysilanol | [C$_6$H$_{13}$O]$_3$SiOH |
| di(sec-butoxy) (2-ethylhexoxy)silanol | [sec-C$_4$H$_9$O]$_2$[C$_8$H$_{17}$O]SiOH |
| di(sec-butoxy) (1,1-dimethylallyloxy)silanol | [sec-C$_4$H$_9$O]$_2$[H$_2$C=CH(CH$_3$)$_2$CO]SiOH |
| di(tert-butoxy) (allyloxy)silanol | [tert-C$_4$H$_9$O]$_2$[CH$_2$=CHCH$_2$O]SiOH |
| tri-phenoxysilanol | [C$_6$H$_5$O]$_3$SiOH |
| tri-(octylphenoxy)silanol | [C$_{14}$H$_{21}$O]$_3$SiOH |

The amidated alkoxysilane cluster reactants of the present invention [represented by formula (III) above] may be prepared by reacting a halogenated alkoxysilane cluster compound with ammonia or the corresponding amine. This reaction is illustrated by the following Equation (B):

R[OSi(OR')$_3$]$_2$X + HNR"R'" →
    R[OSi(OR')$_3$]$_2$NR"R'" + HX     (B)

wherein R, R', R" and R'" are as defined above, and X is a halogen such as chlorine. However, these amidated alkoxysilane cluster reactants may be made by other bly, R" and R'" are the same lower alkyl group having 1 to 4 carbon atoms. Most preferably, both R" and R'" are methyl since dimethylamine will be formed as a co-product with the desired alkoxysilane cluster product (I). Dimethylamine is a preferred co-product since it is volatile, and thus easy to remove from the desired cluster product. The radicals R" and R'" may both by hydrogen for this reaction because undesirable self-condensation side reactions are not likely to occur in the presence of the two sterically hindered alkoxy clusters [OSi(OR')$_3$].

Representative amidated alkoxysilane cluster reactants for the method of the present invention include those named in the following Table (II):

TABLE II
REPRESENTATIVE AMIDATED ALKOXYSILANE CLUSTER COMPOUNDS

| Name | Chemical Formula |
|---|---|
| Bis-(tri-sec-butoxy-silyloxy)-methyl-N,N-dimethylamidosilane | CH$_3$Si[OSi(OC$_4$H$_9$—sec)$_3$]$_2$N(CH$_3$)$_2$ |

TABLE II-continued
REPRESENTATIVE AMIDATED ALKOXYSILANE CLUSTER COMPOUNDS

| Name | Chemical Formula |
| --- | --- |
| Bis-(tri-sec-butoxy-silyloxy)-ethyl-N,N-dimethylamidosilane | $C_2H_5Si[OSi(OC_4H_9\text{—sec})_3]_2N(CH_3)_2$ |
| Bis-(tri-sec-butoxy-silyloxy)-vinyl-N,N-dimethylaminosilane | $CH_2\!\!=\!\!CHSi[OSi(OC_4H_0sec)_3]_2N(CH_3)_2$ |
| Bis-(tri-sec-butoxy-silyloxy)-methyl-N,N-diethylamidosilane | $CH_3Si[OSi(OC_4H_9sec)_3]_2N(C_2H_5)_2$ |
| Bis-(tri-sec-butoxy-silyloxy)-methyl-anilidosilane | $CH_3Si[OSi(CO_4H_9sec)_3]_2NHC_6H_5$ |
| Bis-(tri-sec-butoxy-silyloxy)-methyl-N-methylamidosilane | $CH_3Si[OSi(CO_4H_9sec)_3]_2NHCH_3$ |
| Bis-(tri-sec-butoxy-silyloxy)-amidosilane | $HSi[OSi(OC_4H_9sec)_3]_2NH_2$ |
| Bis-[di(sec-butoxy) (tert-butoxy)silyloxy]-methyl-N,N-dimethylaminosilane | $CH_3Si[OSi(OC_4H_9sec)_2(OC_4H_9tert)]_2N(CH_3)_2$ |
| Bis-[di(sec-butoxy) (2-methyl-3-butene-2-oxy) silyloxy]-methyl-N,N-dimethylamidosilane | $CH_3Si[OSi(OC_4H_9\text{—sec})_2(OC(CH_3)_2CH\!\!=\!\!CH_2)]_2N(CH_3)_2$ |

The mole ratio of the trialkoxysilanol to the amidated alkoxysilane cluster compound as reactants should be at least about 0.8:1 to ensure a desired yield of the alkoxysilane cluster product. Preferably, this mole ratio is in the range of about 0.9:1 to about 1.3:1. Most preferably, this mole ratio is in the range of about 0.95:1 to about 1.05:1.

Suitable temperatures for this type of reaction are generally in the range from about 60° C. to about 200° C. with the preferred range from about 100° C. to about 190° C. and the most preferred range of reaction temperatures from about 130° C. to about 170° C. Of course, the specific temperature preference will depend upon the particular reactants employed. Lower reaction temperatures will usually be employed with relatively more volatile reactants and temperatures may be needed to be increased after the reaction has begun.

The reaction may be carried out in the absence of any above-atmospheric pressure. Sub-atmospheric pressure may be employed to remove any volatile amino co-product and to drive the reaction faster. The reaction is preferably carried out at atmospheric pressure or below that pressure (e.g. from about 760 mm Hg to about 300 mm Hg).

The time of the reaction will depend upon many factors including the reaction temperature and specific reactants employed. Generally, reaction times may vary from about 30 minutes to about 200 minutes or more. However, the present invention is not to be limited to any particular range of reaction times.

Reaction of Equation (A) above may, in some instances, be carried out in the presence of a solvent, but one is not necessary. A solvent may serve to moderate the rate of reaction. Any solvent may be used which dissolves the reactants and does not interfere with reaction of Equation (A).

Once the reaction is substantially complete, as evidenced by a reduction or cessation of the amine evolution, the reaction may be terminated and the alkoxysilane cluster product recovered, preferably by fractional distillation under reduced pressures. Furthermore, the recovered cluster product may be water washed or subjected to other conventional purification techniques besides being distilled.

As stated above, the products of this inventive process are disclosed in U.S. Pat. No. 3,965,136 as having properties which are especially good for functional fluid systems or other applications.

The process of the present invention is illustrated by the following examples. All parts and percentages are by weight unless explicitly stated otherwise.

EXAMPLE 1

PREPARATION OF $H_3C\!\!-\!\!Si[OSi(OC_4H_9sec)_3]_3$

A. STARTING INTERMEDIATE $H_3C\!\!-\!\!Si[OSi(OC_4H_9sec)_3]_2(NCH_3)_2$

A 1000 ml three-necked flask was equipped with a dry ice condenser, thermometer, stirrer, and an equilibrated dropping funnel through which a blanket of $N_2$ could be maintained. The flask was charged with 500 ml low boiling petroleum ether and cooled to $-50°$ with dry ice. In the meantime 64 g dimethylamine were condensed in a flask and weighed (1.41 mole). This amine was quickly poured into the petroleum ether. The dropping funnel had been precharged with 388.3 g cluster chloride $H_3C\!\!-\!\!Si[OSi(OC_4H_9sec)_3]_2Cl$. The purity was 76.5% which is 397 g active compound or 0.49 moles. The major impurity was $H_3CSi[OSi(OC_4H_9sec)_3\text{-}]_2OC_4H_9$ which is difficult to separate from the chloride or amide later on but which does not affect reactions. The $H_3C\!\!-\!\!Si[OSi(OC_4H_9sec)_3]_2Cl$ was dropped into the amine/solvent mixture between $-50°$ and $-30°$ C. The contents were then stirred and the temperature allowed slowly to rise to $+40°$ C. at which point excess amine and lowest boiling portions of petroleum ether began to reflux. Most excess amine boiled off. The dimethylamine hydrochloride was filtered and washed with petroleum ether. The combined filtrate and wash was stripped by distilling the petroleum ether off, last traces in vacuum. 376.5 g crude product was obtained assaying 77.8% by VPC. No distillative purification was possible because the major impurity $H_3C\!\!-\!\!Si[OSi(OC_4H_9sec)_3]_2OC_4H_9$ boils even closer to the amide than to the chloride.

B. PREPARATION OF THE CLUSTER $H_3C\!\!-\!\!Si[OSi(OC_4H_9sec)_3]_3$

A 100 ml three-necked flask was equipped with a magnetic stirring bar, a thermometer, a gas inlet tube and a smaller reflux condenser. The exit of the reflux condenser was attached to a downward leading glass tube which ended in a gas dispersion fritte. The fritte dipped into our Erlenmeyer flask containing 200 ml water and a drop methyl red indicator. A slow stream of $N_2$ was passed through the system to pass the liberated dimethylamine into the absorber. The contents of the flask were now heated in an oil bath.

The following components were heated together: H₃CSi[OSi(OC₄H₉sec)₃]₂N(CH₃)₂ 40 g, assay 77.8%=31.12 g active component or 0.051 mole, and 14.1 g tributoxysilanol assaying 95% (sec C₄H₉O)₃-SiOH or 0.051 mole. The temperature was raised between 105° and 165° within 15 minutes and held at 165° for a total of 90 minutes heating time. After cooling, the crude product was dissolved in 250 ml toluene. To this solution was added 100 ml water and the mixture was stirred overnight. This treatment hydrolyzes traces of unreacted SiN bonds left. The organic phase was separated, washed once with 100 ml water and then dried over magnesium sulfate. After filtration, the solvent was vacuum stripped. After this work-up, there was obtained 47.2 g crude product assaying 67% cluster, which was a 74.8% yield. After fractionation on a micro Vigreux column, there was obtained 25.3 g cluster H₃CSi[OSi(OC₄H₉sec)₃]₃ bp 192°/0.05 mm Hg.

The physical properties of the cluster were identical with those of products prepared by the conventional cluster synthesis described in U.S. Pat. No. 3,965,136.

EXAMPLE 1A

LARGE SCALE PREPARATION OF THE INTERMEDIATE H₃C—Si[OSi(OC₄H₉sec)₃]₂N(CH₃)₂

With this method the intermediate chloride H₃C—Si[OSi(OC₄H₉sec)₃]₂Cl is not isolated.

A 2 liter three-necked flask was equipped with a condenser, stirrer, thermometer, and an equilibrated dropping funnel through which a blanket of dry N₂ could be maintained. The flask was charged with 31.6 g methyltrichlorosilane CH₃SiCl₃ (0.211 moles) and 420 ml toluene. The solution was cooled to −10° C. A solution of 115.2 g tri-sec-butoxysilanol (assay 97%)=0.423 mole and 33.5 g pyridine (0.423 mole) and 50 ml toluene was added dropwise over a 3 hr. period. The temperature rose to −6° during the addition. To complete the intermediate step the mixture was heated 2 hrs. to 60° C. A VPC showed 76.3% chlorointermediate (on a solvent-free basis). The mixture was cooled with ice for 1 hr. to allow the pyridine hydrochloride to decrease in solubility. This salt was now filtered and washed with 80 ml toluene. The filtrate and wash were returned to the three-necked flask (traces of pyridine hydrochloride left do not interfere) and cooled to −12°. In the meantime, 26 g dimethylamine HN(CH₃)₂ (0.577 mole) was condensed in a flask and a gas inlet tube was installed in the reactor and attached to the flask containing dimethylamine. The dimethylamine was vaporized over a 40 min. period and the vapors passed into the reaction flask. The dimethylamine was in excess over the theoretically required 0.422 mole to compensate for possible incomplete absorption. When all dimethylamine was added, the cooling bath was removed and the reactants allowed to warm up to room temperature overnight. A slow sparge of dry nitrogen was bubbled through the reactants during this period. The dimethylamine hydrochloride was filtered and washed with 80 ml toluene. The combined filtrate and wash was vacuum stripped leaving 123.4 g crude product.

The crude product was fractionated on a Vigreux column (bp 170°-171° C. at 0.09 mm Hg) and obtained in 97% purity by VPC. However, any co-product H₃C—Si[OSi(OC₄H₉sec)₃]₂OC₄H₉ sec present cannot be distinguished or separated by VPC.

For synthesis work the vacuum-stripped product is adequate, especially when the final products are purified by fractionation.

EXAMPLE 2

PREPARATION OF H₃C—Si[OSi(OC₄H₉sec)₃]₃ FROM H₃C—Si[OSi(OC₄H₉sec)₃]₂NH₂ INTERMEDIATE AND TRI-SEC-BUTOXY SILANOL This example shows the preparation of the alkoxysilane cluster using the alkoxysilyamide as intermediate.

A 1 liter three-necked flask, equipped with stirrer reflux condenser, thermometer and gas inlet tube was charged with 293.5 g cluster chloride assaying 77.22% H₃CSi[OSi(OC₄H₉sec)₃]₂Cl or 226.6 g active product (0.374 mole) in 300 ml n heptane. The mixture was cooled to 0° and 25 g ammonia was bubbled through the reaction mixture in 1.5 hrs. This is an excess over the theoretically required 0.748 mole (12.74 g). The reaction mixture was warmed to 40° C. and N₂ was bubbled through to remove most of the ammonia. The ammonium chloride was filtered and the solvent of the filtrate vacuum stripped leaving 267 g product assaying 74.56% by VPC. This represented a yield of 199.07 g H₃CSi[OSi(OC₄H₉sec)₃]₂NH₂ (0.34 mole 90.7% yield).

To this product, transferred into an apparatus described in Example 1, Step B was added 104.1 g silanol, assay 95.07% (s.C₄H₉O)₃SiOH by VPC or 0.34 mole. During 4 hrs. at 180°–200°, 92% of the ammonia had been released; the remainder escaped during 12 hrs. heating to 160°.

After taking the product up in 400 ml n heptane and the usual hydrolysis and wash procedure there was obtained 343.3 g crude product containing 68.59% H₃C—Si[OSi(OC₄H₉sec)₃]₃. This was 235.4 g or an 83.17% yield. Vacuum fractionation on a spinning band column gave 151.9 g product of 99% purity (bp 194° at 0.07 mm Hg). This was a 65.6% in-hand yield of pure product.

The physical properties of the cluster were identical with product from Example 1, Step B or samples prepared via the conventional cluster synthesis shown in U.S. Pat. No. 3,965,136.

EXAMPLE 3

PREPARATION OF H₂C=CHSi[OSi(OC₄H₉sec)₃]₂OSi(OC₄H₉sec)₂OC(CH₃)₂CH=CH₂

Following the procedure of Example 1, Step B 66.31 g HOSi(OC₄H₉sec)₂OC(CH₃)₂CH=CH₂, 98% assay=0.235 mole was reacted with 161.72 g cluster amide of the formula H₂C=CHSi[OSi(OC₄H₉)₃]₂N(CH₃)₂ (assay 91% by VPC=147.17 g or 0.235 mole) 1 hr. to 170°. (The vinyl cluster amide was analogous prepared according to Example 1, Step A, but using H₂C=CHSi[OSi(OC₄H₉sec)₃]₂Cl and dimethylamine as reactant). After the usual work-up there was obtained 206.1 g crude material with a VPC purity of 90%. The low boilers were stripped in high vacuo. The refractive index of the product was 1.4266 and the following analysis data were obtained:

| Analysis for Si₄C₃₉H₈₄O₁₂ (MW 857.433) | |
|---|---|
| Calculated | Found |
| C   54.63% | C   53.8% |

| Analysis for $Si_4C_{39}H_{84}O_{12}$ (MW 857.433) | | | |
|---|---|---|---|
| Calculated | | Found | |
| H | 9.88% | H | 9.56% |
| Si | 13.10% | Si | 12.72% |

EXAMPLE 4

PREPARATION OF
$H_3C-Si[OSi(OC_4H_9sec)_3]_2[OSi(OC_4H_9sec)_2OC(CH_3)_2CH=CH_2]$ This example demonstrates the preparation of a cluster with one unsaturation on one trialkoxysilane group.

Following the procedure of Example 1, Step B, 66.2 g (2-methyl-3-butene-2-oxy)-di-sec-butoxysilanol of the formula $HOSi(OC_4H_9sec)_2OC(CH_3)_2CH=CH_2$, assay 96.5% = 0.231 mole was reacted with 155.5 g bis-(tri-sec-butoxy-silyloxy)-methyl-N,N-dimethylamidosilane of the formula $H_3CSi[OSi(OC_4H_9sec)_3]_2N(CH_3)_2$ (assay 91.2% = 141.8 g or 0.231 mole) for 60 minutes at 130° and 75 minutes at 160° C.

After the usual work-up there was obtained 248 g crude product (containing some toluene). Fractionation on a micro Vigreux column in vacuum gave 136.2 product in 99.3% purity which is a 69.3% in-hand yield, while the yield of product formed in all cuts was 74.3%. The boiling point was 180°–185° C. at 0.05 mm Hg.

| Analysis for $Si_4C_{38}H_{84}O_{12}$ (MW 845.422) | | | |
|---|---|---|---|
| Calculated | | Found | |
| C | 53.98% | C | 53.8% |
| H | 10.02% | H | 9.89% |
| Si | 13.29% | Si | 12.71% |

EXAMPLE 5

PREPARATION OF
$H_3C-Si[OSi(OC_4H_9sec)_2OC(CH_3)_2CH=CH_2]_2[OSi(OC_4H_9sec)_3]$ This example demonstrates the preparation of a cluster with two unsaturations on two trialkoxysilane groups.

Following the procedure in Example 1A, but using 2 moles (2-methyl-3-butene-2-oxy)-di(sec-butoxy)silanol per mole methyl trichlorosilane and reacting the corresponding chloride imtermediate with dimethylamine afforded the precursor bis-[di(sec-butoxy)(2-methyl-3-butene-2-oxy)silyloxy]-methyl-N,N-dimethylamidosilane of the formula $H_3C-Si[OSi(OC_4H_9sec)_2(OC(CH_3)_2CH=CH_2)]_2N(CH_3)_2$ Following the procedure of Example 1, Step B, 41.86 g tri-sec-butoxysilanol of the formula $HOSi(OC_4H_9sec)_3$, assay 91.6% = 0.145 mole was reacted with 155.5 g amide precursor (assay 94.6% by VPC=0.145 mole) for 80 mins. at temperatures starting at 150° C. and ending at 180° C., after which time the dimethylamine was expelled. 130.8 g crude material with a VPC purity of 81.6% was obtained.

The crude product was distilled without going through the wash procedure. The purest cut weighed 79.3 g and boiled at 192°–197° C. at 0.1 mm Hg (VPC purity 94.4%). This represents an in-hand yield of 58%.

| Analysis for $Si_4C_{39}H_{84}O_{12}$ (MW 857.433) | | | |
|---|---|---|---|
| Calculated | | Found | |
| C | 54.63% | C | 55.18% |
| H | 9.88% | H | 9.66% |
| Si | 13.10% | Si | 11.99% |

EXAMPLE 6

PREPARATION OF
$H_2C=CHSi[OSi(OC_4H_9)_2OC(CH_3)_2CH=CH_2]_2[OSi(OC_4H_9sec)_3]$ This example demonstrates the preparation of a cluster containing two unsaturations in the shell and one unsaturation on the central silicon atom.

The precursor bis-[di(sec-butoxy)(2-methyl-3-butene-2-oxy)silyloxy]-vinyl-N,N-dimethylamidosilane $H_2C=CHSi[OSi(OC_4H_9sec)_2(OC(CH_3)_2CH=CH_2)]_2N(CH_3)_2$ was prepared by the method shown in Example 1A from vinyltrichlorosilane, (2-methyl-3-butene-2-oxy)-di(sec-butoxy)silanol and dimethylamine.

Following the procedures in Example 1, Step B, 18.58 g tri(sec-butoxy)silanol of the formula $HOSi(OC_4H_9sec)_3$, 91.6% assay = 0.058 moles was reacted with 38.8 g amide precursor, assay 96.7%, 0.058 moles for 2 hrs. at 130°–150° C. After the wash, there was obtained 50.25 g material, showing a 77.3% assay by VPC. Fractionation through a micro Vigreux column gave 33.21 g product of 94.1% purity, bp 175°–177° C. at 0.07 mm Hg. This represents a 63.2% in-hand yield.

| Analysis for $Si_4C_{40}H_{84}O_{12}$ (MW 869.444) | | | |
|---|---|---|---|
| Calculated | | Found | |
| C | 55.26% | C | 55.58, 55.61% |
| H | 9.74% | H | 9.43, 9.32% |
| Si | 12.92% | Si | 12.96, 11.3% |

What is claimed is:

1. A process for preparing an alkoxysilane cluster compound of the formula:

$RSi[OSi(OR')_3]_3$ wherein R is hydrogen, alkyl, alkenyl, aryl, aralkyl; each R' is independently selected from the same group as R subject to a proviso that at least a majority of said R' radicals are sterically hindered alkyl groups having at least 3 carbon atoms;

comprising reacting a trialkoxysilanol of the formula:

$HOSi[OR']_3$ wherein R' is defined above, with an amidated alkoxysilane cluster compound of the formula:

$RSi[OSi(OR')_3]_2NR''R'''$ wherein R and R' are defined above, and R" and R''' are individually selected from hydrogen, lower alkyl groups having 1-4 carbon atoms and phenyl;

employing at least 0.8 moles of said trialkoxysilanol per one mole of said amidated alkoxysilane cluster compound;

and said reaction being carried out at about 60° C. to about 200° C.

2. The process of claim 1 wherein said R radical is either hydrogen, an alkyl or an alkenyl having 1 to 24 carbon atoms, or an aryl or an aralkyl having from about 6 to about 24 carbon atoms.

3. The process of claim 1 wherein said R' radicals are individually selected from hydrogen, alkyl or alkenyl groups having 1 to about 18 carbon atoms, or aryl or aralkyl groups having about 6 to about 24 carbon atoms, subject to said proviso.

4. The process of claim 1 wherein said R" and R'" are selected from either hydrogen or a lower alkyl group from 1 to 4 carbon atoms.

5. The process of claim 1 wherein said mole ratio of said trialkysilanol to said amidated alkoxysilane cluster compound is in the range of about 0.9:1 to about 1.3:1.

6. The process of claim 1 wherein said reaction temperature is in the range from about 100° C. to about 190° C.

7. The process of claim 1 wherein said R radical is either hydrogen, an alkenyl group having 1 to about 8 carbon atoms, or an aryl or aralkyl group having about 6 to about 14 carbon atoms and said R' radicals are all sterically hindered alkyl groups having 4 to about 12 carbon atoms.

8. The process of claim 7 wherein R" and R'" are the same lower alkyl group having 1 to 4 carbon atoms.

9. The process of claim 8 wherein R is methyl, the R' radicals are all sec-butyl, and R" and R'" are both methyl.

* * * * *